United States Patent [19]

Tordeux et al.

[11] Patent Number: 4,855,460
[45] Date of Patent: Aug. 8, 1989

[54] PROCESS FOR PERFLUOROALKYLATION OF ACID ANHYDRIDES

[75] Inventors: Marc Tordeux, Sceaux; Claude Wakselman, Paris; Catherine FRancese, L'Hay Les Roses, all of France

[73] Assignee: Rhone-Poulenc Chimie, Courbevoie, France

[21] Appl. No.: 217,338

[22] Filed: Jul. 11, 1988

[30] Foreign Application Priority Data

Jul. 10, 1987 [FR] France ................................ 87 10176

[51] Int. Cl.$^4$ ...................... C07C 29/00; C07C 45/00; C07D 307/32; C07D 307/88
[52] U.S. Cl. .................................. 549/308; 549/281; 549/300; 549/324; 568/303; 568/308; 568/319; 568/335; 568/354; 568/376; 568/380; 568/381; 568/397; 568/416; 568/419; 568/647; 568/683; 568/700; 568/812; 568/822; 568/838; 568/834; 568/842
[58] Field of Search ............... 549/281, 300, 308, 324; 568/303, 308, 319, 335, 354, 376, 380, 381, 397, 416, 419, 647, 683, 700, 812, 822, 838, 839, 842

[56] References Cited

U.S. PATENT DOCUMENTS 3,236,894  2/1966  England .............................. 260/574

OTHER PUBLICATIONS

"An Efficient Synthesis of 3-Hydroxy-3-Trifluoromethyl Phthalide", Donald A. Shaw & Terrence C. Tuominen, Synthetic Communications, 15(14), 1291–1297 (1985).

"Regiospecific Synthesis of Aromatic Compounds via Organometallic Intermediates", Prahbu, Eapen & Tamborski, J. Org. Chem., 1984, 49, 2792–2795.

Primary Examiner—Richard L. Raymond
Attorney, Agent, or Firm—Finnegan, Henderson, Farabow, Garrett & Dunner

[57] ABSTRACT

A process for the preparation of perfluoroalkylated ketones and/or perfluoroalkylated alcohols, comprising the step of contacting a perfluoroalkyl iodide or perfluoroalkyl bromide with an acid anhydride, in the presence of a metal chosen from zinc and cadmium.

16 Claims, No Drawings

PROCESS FOR PERFLUOROALKYLATION OF ACID ANHYDRIDES

FIELD OF THE INVENTION

The present invention relates to a new process for the preparation of perfluoroalkylated ketones or perfluoroalkylated alcohols. Specifically, it relates to a process for perfluoroalkylation of acid anhydrides.

BACKGROUND OF THE INVENTION

It is known, for example, according to the paper by Donald A. Shaw and Terrence C. Tuominen, which appeared in Synthetic Communications 15(14), 1291–1297 (1985), to prepare 3-hydroxy-3-trifluoromethyl phthalide, which can be used as a plant growth regulator, in three stages. The starting materials employed are bromotoluene and an amide of trifluoroacetic acid, of the formula $CF_3CONCH_3(OCH_3)$, in the presence of magnesium in ether. The starting materials, especially the amide of trifluoroacetic acid, are not readily available. In addition, industry has always been reluctant to use a highly reactive magnesium derivative because of process economy and safety aspects.

It is also known, according to a paper by Prabhu, Eapen and Tamborski, which appeared in J. Org. Chem. 1984, 49, 2792–2795, to prepare the same product as in the preceding paper by a different process. The process according to this paper starts with a dibromo derivative which is condensed with butyllithium at $-110°$ C. The use of alkyllithium derivatives, however, has always been avoided in industry for safety reasons, as these derivatives are highly flammable.

Thus, industry continues to search for a process which is economically satisfactory, and secure with regard to safety, for preparing the various prefluorinated ketones and alcohols required by the agrochemical and pharmaceutical industries.

DESCRIPTION OF THE INVENTION

The present invention has made it possible to attain this objective, long sought after by industry: to provide a secure, relatively nonhazardous and economical process for preparing perfluorinated ketones and alcohols.

The present invention relates to a process for perfluoroalkylation of acid anhydrides by bringing a perfluoroalkyl iodide or perfluoroalkyl bromide into contact with an acid anhydride in the presence of a metal chosen from zinc and cadmium.

In the present invention, the term acid anhydride preferably includes three classes of compounds:

(1) anhydrides of straight-chain or branched-chain aliphatic monoacids
(2) anhydrides of diacids, and
(3) anhydrides of aromatic monoacids.

Preferred anhydrides of straight-chain or branched-chain aliphatic monoacids include anhydrides of monoacids containing 1 to 8 carbon atoms, optionally substituted by an alkoxy group containing 1 to 2 carbon atoms, by a phenoxy group, by an aralkyl group or by a cycloalkyl group containing 3 to 6 carbon atoms. Still more preferred are anhydrides of straight-chain aliphatic monoacids containing 1 to 4 carbon atoms, most preferably acetic anhydride. Exemplary acid anhydrides of this first class include:

the anhydrides of α- and β-methoxy- or -ethoxybutyric acids
the anhydrides of methoxy- or ethoxypropionic acids
the anhydrides of methoxy- and ethoxyacetic acids
phenoxybutyric anhydride
phenoxypropionic anhydride
phenoxyacetic anhydride
butyric anhydride
isobutyric anhyride
cyclohexylbutyric anhydride
cyclohexylpropionic anhydride
cyclohexylacetic anhydride
cyclohexylcarboxylic anhydride
the anhydrides of cyclopentylbutyric, -propionic, -acetic and -carboxylic acids
the anhydrides of cyclopropylbutyric, -propionic, -acetic and -carboxylic acids
phenylacetic anhydride, and the anhydrides of phenylbutyric and -propionic acids.

Exemplary diacid anhydrides include saturated or unsaturated mono- or polycyclic diacid anhydrides. It is preferred to employ succinic anhydride or phthalic anhydride.

Acid anhydrides of this second class may include:
succinic anhydride
glutaric anhydride
cyclohexanedicarboxylic anhydride
5-norbornene-2,3-dicarboxylic anhydride
maleic anhydride
citraconic anhydride
naphthalenedicarboxylic anhydride
phthalic anhydride, and
1,2,3,6-tetrahydrophthalic anhydride.

The anhydrides of aromatic monoacids may include anhydrides of mono- or polycyclic monoacids optionally substituted by a fluorine or chlorine atom, an alkoxy group containing 1 to 2 carbon atoms, an alkyl group containing 1 to 2 carbon atoms or a trifluoromethyl group.

Exemplary acid anhydrides of this third class may include:
benzoic anhydride
anisic anhydride
fluorobenzoic anhydride, and toluic anhydride, the above compounds having the carboxyl group which forms the anhydride directly attached to a phenyl ring.

The perfluoroalkyl iodides or perfluoroalkyl bromides are preferably chosen from trifluoromethyl bromide and perfluoroalkyl iodides whose perfluorinated alkyl chain contains 2 to 12 carbon atoms. This preference is not due to a difference in the reactivity of the bromo or iodo compounds, but solely due to a cost difference. In fact, bromotrifluoromethane is much less expensive than iodotrifluoromethane and, conversely, perfluoroalky iodides such as perfluoroethyl and perfluorobutyl iodides are much less expensive than their bromide analogs.

To make the invention easier to employ, a polar aprotic solvent and/or a pyridine are/is employed.

The polar aprotic solvents are preferably chosen from:
dimethylformamide
dimethylacetamide
N-methylpyrrolidone.

The pyridines employed may be substituted or unsubstituted. It is preferred to employ pyridine and methylpyridine.

Among all these solvents, it is preferred to employ dimethylformamide and/or pyridines.

In a preferred embodiment of the invention, a ratio (atom/mole) of the metal, zinc or cadmium, to the anhydride which is greater than or equal to 1 and lower than or equal to 2, and a molar ratio of the perfluoroalkyl iodide or perfluoroalkyl bromide to the anhydride which is greater than or equal to 1, are employed. If the perfluoroalkyl halide is used in excess, and the perfluoroalkyl halide employed is bromotrifluoromethane, the latter will be easily recycled, since it is in the form of a gas.

For better implementation of the reaction, it is preferable to maintain a temperature below 115° C., and still more preferable to maintain a temperature of from 20° to 70° C.

The pressure is preferably higher than atmospheric pressure when the perfluoroalkyl halide is gaseous and, more preferably, from 1 to 15 bars.

The operation is preferably carried out in the absence of oxygen.

Products which may be obtained by the process of the present invention include:
1,1,1-trifluoroacetone
1,1,1,3,3,3-hexafluoro-2-methyl-2-propanol
1,1,1-trifluoro-2-pentanone
3-hydroxy-3-trifluoromethyl-1-isobenzofuranone
3-hydroxy-3-(tridecafluror-n-hexyl) (3H)-1-isobenzofuranone
5,5-bis(trifluoromethyl)tetrahydro-2-furanone, and
5-hydroxy-5-trifluoromethyltetrahydro-2-furanone.

The products obtained by the process of the invention may be employed, in particular, as active agents for regulating plant growth, or as transformer fluids (U.S. Pat. No. 3,236,894).

The invention is described more completely with the aid of the following examples, which should not be considered as limiting the invention.

EXAMPLE 1:

ACETIC ANHYDRIDE - Zn -CF$_3$Br 25 ml of dimethylformamide, 5 ml of acetic anhydride (0.053 mole) and 5 g of zinc powder (0.077 mole) were placed in a thick glass flask.

The flask was placed in a Parr apparatus. This was evacuated, and then bromotrifluoromethane was introduced up to a pressure of 3.6 bars. The flask was agitated during the reaction period, the pressure being maintained between 4 and 2.5 bars.

The 1,1,1-trifluoroacetone obtained was identified by $^{19}$F NMR, and the yield determined after addition of 2,2,2-trifluoroethanol to the crude for handling. It amounted to 26%. $^{19}$F NMR (CFCl$_3$ ext.) =-79 ppm (s, CF$_3$)

EXAMPLE 2:

ACETIC ANHYDRIDE - Cd - CF$_3$Br 25 ml of pyridine, 10 ml of acetic anhydride (0.11 mole) and 12 g of cadmium powder (0.11 mole) were placed in a thick glass flask.

The flask was placed in a Parr apparatus. This was evacuated, and then bromotrifluoromethane was introduced up to a pressure of 3.6 bars. The flask was agitated during the reaction period, the pressure being maintained between 4 and 2.5 bars.

The 1,1,1,3,3,3-hexafluoro-2-methyl-2-propanol product obtained was identified by $^{19}$F NMR. $^{19}$F NMR (CFCl$_3$ ext.)=−80.3 ppm (q, CF$_3$)

EXAMPLE 3:

BUTYRIC ANHYDRIDE - Zn - CF$_3$Br 10 ml of butyric anhydride (0.061 mole), 25 ml of pyridine and 6 g of zinc powder (0.092 mole) were placed in a thick glass flask.

The flask was placed in a Parr apparatus. This was evacuated, and then bromotrifluoromethane was introduced up to a pressure of 3.6 bars. The flask was agitated throughout the reaction period, the pressure being maintained between 4 and 2.5 bars.

The mixture was filtered, and then hydrolyzed and 30 ml of ice-cold 10% hydrochloric acid with stirring for 30 minutes.

After extraction with ether, washing with water, drying over magnesium sulfate and evaporation of the solvent, the 1,1,1-trifluoro-2-pentanone was distilled:
b.p. =70–74° C. The yield amounted to 20%.
$^{19}$F NMR (CFCl$_3$ ext.)=−76 ppm (s, CF$_3$)
$^1$H NMR (TMS int.)=2.3 ppm (q, CH$_2$)
1.7 ppm (sext., CH$_2$)
1 ppm (t, CH$_3$)

EXAMPLE 4:

PHTHALIC ANHYDRIDE - Zn - CF$_3$Br 5 g of phthalic anhydride (0.034 mole), 40 ml of pyridine and 4 g of zinc powder (0.062 mole) were placed in a thick glass flask.

The flask was placed in a Parr apparatus. This was evacuated, and then bromotrifluoromethane was introduced up to a pressure of 3.6 bars. The flask was agitated throughout the reaction period, the pressure being maintained between 4 and 2.5 bars.

The mixture was filtered and then hydrolyzed with 50 ml of ice-cole 10% hydrochloric acid with stirring for 30 minutes.

After extraction with chloroform, washing with water, drying over magnesium sulfate and evaporation of the solvent, the 3-hydroxy-3-trifluoromethyl (3H)-1-isobenzofuranone was distilled under reduced pressure:
b.p.=80°–90° C./7.6×10$^{-3}$ mm Hg.

The yield was 4.5 g (61%); m.p.=98.2° C. (literature m.p.=98–100° C.).
$^{19}F$ NMR (CFCl$_3$etx.)=−82 ppm (s, CF$_3$)
$^1$H NMR (TMS int.)=8−7.5 ppm (m, Ar) 4.4 ppm (OH)
$^{13}$C NMR (TMS int.)=167.05 ppm (C=0) 141.6−135.5−132.4−126.7−126.07−124.03 ppm (C - Ar) 117.8 ppm (q, CF$_3$, J=280 Hz) 100.3 ppm (q, C - CF$_3$, J=35 Hz)

IR (KBr)=3350 cm$^{-1}$ (OH) 1765 cm$^{-1}$ (C=O) 1605 cm$^{-1}$ (C=C-Ar)

Mass m/e=218 (M$^+$), 201 (M$^+$- OH), 149 (M$^+$- CF$_3$)

EXAMPLE 5:

PHTHALIC ANHYDRIDE - Cd - CF$_3$Br 5 g of phthalic anhydride (0.0338 mole), 40 ml of pyridine and 5 g of cadmium powder (0.0446 mole) were placed in a thick glass flask.

The remaining procedure was as in Example 4.

3.7 g of 3-hydroxy-3-trifluoromethyl (3H)-1-isobenzofuranone (50%) were obtained.

EXAMPLE 6:

PHTHALIC ANHYDRIDE - Zn - $C_6F_{13}I$ 20 ml of pyridine, 3 g of phthalic anhydride (0.021 mole) and 2 g of zinc powder (0.031 mole) were placed in a round-bottomed flask.

This was puged with argon and 10 g of 1-iodoperfluoro-n-hexane (0.0224 mole) were then added with stirring.

The mixture was filtered and then hydrolyzed with 20 ml of ice-cold 10% hydrochloric acid with stirring for 30 minutes.

After extraction with chloroform, washing with water, drying over magnesium sulfate and evaporation of the solvent, the 3-hydroxy-3-(tridecafluoro-n-hexyl) (3H)-1-isobenzofuranone obtained was distilled under reduced pressure:

b.p. = 94° C./4×10⁻² mm Hg.

2 g (21%) of product which crystallizes were obtained:

m.p. = 107.3° C.

$^{19}F$ NMR ($CFCl_3$ ext.) = −81.3 ppm (E, $CF_3$): −118.7 to −128.3 ppm (m, 10 F).

$^1H$ NMR (TMS int.) = 8−7.5 ppm (m, 4H Ar); 4.3 ppm (OH).

EXAMPLE 7:

SUCCINIC ANHYDRIDE - Zn - $CF_3Br$ 5 g of succinic anhydride (0.05 mole), 50 ml of pyridine and 4 g of zinc powder (0.0615 mole) were placed in a thick glass flask.

The flask was placed in a Parr apparatus. This was evacuated, and then bromotrifluoromethane was introduced up to a pressure of 3.6 bars. The flask was agitated throughout the reaction period, the pressure being maintained between 4 and 2.5 bars.

The mixture was filtered, and then hydrolyzed with 50 ml of ice-col 10% hydrochloric acid with stirring for 30 minutes.

After extraction with ether, washing with water, drying over magnesium sulfate and evaporation of the solvent, the two products obtained were separated by gas phase chromatography (column: 30% SE 30 on Chromosorb PAW 45/60 mesh) at 140° C.

These two products were 5,5-bis(trifluoromethyl)tetra-hydro-2-furanone and 5-hydroxy-5-trifluoromethyl-tetrahydro-2-furanone, in yields of 40% and 18%, respectively.

5,5-Bis(trifluoromethyl)tetrahydro-2-furanone

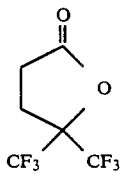

$^{19}F$ NMR ($CFCl_3$ ext.):
−77.3 ppm (s, $CF_3$)
$^1H$ NMR (TMS int.):
3−2.4 ppm (m, $CH_2$—$CH_2$)
$^{13}C$ NMR (TMS int.)
172.8 ppm (C=O)
122.2 ppm (q, $CF_3$, J=285 Hz) $CF_3$
80.8 ppm (sept. C, J=32 Hz) $CF_3$
26.2 ppm and 23.2 ppm ($CH_2$, $CH_2$)

5-Hydroxy-5-trifluoromethyltetrahydro-2-furanone

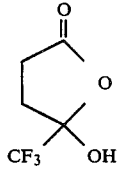

$^{19}F$ NMR ($CFCl_3$ ext.):
−84.7 ppm (s, $CF_3$)
$^1H$ NMR (TMS int.):
6 ppm (OH)
3.2−2.1 ppm (m, $CH_2$—$CH_2$)
$^{13}C$ NMR (TMS int.):
176.04 ppm (C=O)
122 ppm (q, $CF_3$, J=287 Hz)
102.3 ppm (q, C-$CF_3$, J=35 Hz)
28.5 ppm and 27.8 ppm ($CH_2$—$CH_2$)

EXAMPLES 8-11

The following table recites the starting anhydrides, operating conditions, products obtained and yields thereof for Examples 8 to 11. Bromotrifluoromethane was employed as the perfluoroalkyl halide in Examples 8 to 11.

| Ex | Starting anhydride | Operating conditions | Products obtained | Yield |
|---|---|---|---|---|
| 8 | Benzoic anhydride | 15 g (0.064 mole) 25 ml pyridine or DMF | $CF_3$—C(=O)—Ph | 5% |
|  | $(PhCO)_2O$ | 5 g Zn (0.077 mole) 20° C. | $CF_3$, Ph, $CF_3$, OH on C | 10% |
| 9 | Naphthalic anhydride | 5 g (0.025 mole) 50 ml pyridine 3 g Zn (0.046 mole) 20° C. | (naphthalene with C=O and C($CF_3$)(OH)) | 10% |

| | Starting | Operating | Products | |
|---|---|---|---|---|
| Ex | anhydride | conditions | obtained | Yield |
| 10 | Maleic anhydride  | 10 g (0.102 mole) 25 ml pyridine or DMF 7 g Zn (0.108 mole) 20° C. | | 5% |
| 11 | Citraconic anhydride | 5 g (0.045 mole) 25 ml pyridine 3.5 g Zn (0.054 mole) 20° C. | | 5% 5% |

We claim:

1. A process for the perfluoroalkylation of an acid anhydride, comprising the step of contacting a perfluoroalkyl iodide or a perfluoroalkyl bromide with an acid anhydride, in the presence of a metal chosen from zinc and cadmium.

2. The process of claim 1, wherein said perflurooalkyl iodide or perfluoroalkyl bromide corresponds to the formula:

$$X(CF_2)_n F$$

wherein n is from 1 to 12 and X denotes Br when n=1 and X denotes I when n is from 2 to 12.

3. The process of claim 1, wherein said acid anhydride is chosen from anhydrides of straight-chain or branched chain aliphatic monoacids, diacid anhydrides and anhydrides of aromatic monoacids.

4. The process of claim 3, wherein said straight-chain or branched-chain aliphatic monoacid anhydrides contain 1 to 8 carbon atoms and are optionally substituted by an alkoxy group containing 1 to 2 carbon atoms, by a phenoxy group, by an aralkyl group or by a cycloalkyl group containing 3 to 6 carbon atoms.

5. The process of claim 4, wherein said straight-chain aliphatic monoacid anhydrides contain 1 to 4 carbon atoms.

6. The process of claim 3, wherein said diacid anhydrides are chosen from saturated or unsaturated mono- or polycyclic diacid anhydrides.

7. The process of claim 6, wherein said diacid anhydrides are chosen from the anhydrides of saturated acids selected from the group consisting of succinic, glutaric and cyclohexanedicarboxylic acids and from the anhydrides of unsaturated acids selected from the group consisting of maleic, citraconic and phthalic acids.

8. The process of claim 3, wherein said anhydrides of aromatic monoacids are chosen from anhydrides of mono- or polycyclic monoacids, optionally substituted by a fluorine or chlorine atom, an alkoxy group containing 1 to 2 carbon atoms, an alkyl group containng 1 to 2 carbon atoms or a trifluoromethyl group.

9. The process of claim 8, wherein said anhydrides of aromatic monoacids are chosen from optionally substituted anhydrides of benzoic and naphthalenic acids.

10. The process of claim 1, wherein said acid anhydride is chosen from acetic anhydride, phthalic anhydride and succinic anhydride.

11. The process of claim 1, wherein a solvent chosen from pyridines and polar aprotic solvents is employed.

12. The process of claim 11, wherein said solvent is chosen from dimethylformamide, dimethylacetamide and N-methylpyrrolidone.

13. The process of claim 1, wherein the ratio of the number of gram-atoms of said metal to the number of moles of said perfluoroalkyl iodide or perfluoroalkyl bromide is from 1:1 to 2:1.

14. The process of claim 1, wherein the ratio of the number of moles of said perfluoroalkyl iodide or perfluoroalkyl bromide to the number of moles of said acid anhydride is greater than or equal to 1:1.

15. The process of claim 1, wherein the reaction temperature ranges from 20° to 70° C.

16. The process of claim 1, wherein said contacting step is conducted for a time sufficient to obtain a perfluoroalkylated ketone and/or a perfluoroalkylated alcohol.

* * * * *